United States Patent
Shao et al.

(10) Patent No.: US 11,045,101 B2
(45) Date of Patent: Jun. 29, 2021

(54) DEVICE AND METHOD FOR REMOVAL OF ARTIFACTS IN PHYSIOLOGICAL MEASUREMENTS

(71) Applicant: Nitto Denko Corporation, Osaka (JP)

(72) Inventors: Shiyun Sunny Shao, Singapore (SG); Kittipong Kasamsook, Singapore (SG)

(73) Assignee: Nitto Denko Corporation, Osaka (JP)

( * ) Notice: Subject to any disclaimer, the term of this patent is extended or adjusted under 35 U.S.C. 154(b) by 539 days.

(21) Appl. No.: 15/538,855

(22) PCT Filed: Dec. 23, 2014

(86) PCT No.: PCT/SG2014/000615
§ 371 (c)(1),
(2) Date: Jun. 22, 2017

(87) PCT Pub. No.: WO2016/105275
PCT Pub. Date: Jun. 30, 2016

(65) Prior Publication Data
US 2017/0347901 A1    Dec. 7, 2017

(51) Int. Cl.
*A61B 5/02* (2006.01)
*A61B 5/024* (2006.01)
*A61B 5/00* (2006.01)

(52) U.S. Cl.
CPC .......... *A61B 5/02416* (2013.01); *A61B 5/681* (2013.01); *A61B 5/6824* (2013.01); *A61B 5/721* (2013.01); *A61B 5/7239* (2013.01)

(58) Field of Classification Search
CPC ... A61B 5/02416; A61B 5/6824; A61B 5/681; A61B 5/721; A61B 5/7239
See application file for complete search history.

(56) References Cited

U.S. PATENT DOCUMENTS

| | | | |
|---|---|---|---|
| 8,573,982 B1 * | 11/2013 | Chuang | G09B 19/0038 434/255 |
| 8,938,291 B1 * | 1/2015 | Azarnasab | A61B 5/04017 327/551 |

(Continued)

FOREIGN PATENT DOCUMENTS

| | | |
|---|---|---|
| CN | 101400296 A | 4/2009 |
| CN | 102573618 A | 7/2012 |

(Continued)

OTHER PUBLICATIONS

International Search Report for International Application No. PCT/SG2014/000615, "Device and Method for Removal of Artifacts in Physiological Measurements", dated Feb. 18, 2015.

(Continued)

*Primary Examiner* — Navin Natnithithadha
*Assistant Examiner* — Andrey Shostak
(74) *Attorney, Agent, or Firm* — Hamilton, Brook, Smith & Reynolds, P.C.

(57) ABSTRACT

A method and device for removal of artifacts in physiological measurements. The method comprising the steps of obtaining a physiological signal of a user; obtaining corresponding motion data representative of motion of the user; detecting two or more motion cycles in the motion data; constructing a noise reference based on segments of the physiological signal corresponding to the two or more motion cycles respectively, and filtering the physiological signal with the noise reference.

18 Claims, 9 Drawing Sheets

(56) References Cited

U.S. PATENT DOCUMENTS

| | | | |
|---|---|---|---|
| 2007/0073170 A1 | 3/2007 | Danehorn et al. | |
| 2009/0326831 A1* | 12/2009 | McGonigle | A61B 5/726 702/19 |
| 2011/0066381 A1 | 3/2011 | Garudadri et al. | |
| 2011/0098608 A1* | 4/2011 | Griffiths | A61B 5/1114 600/595 |
| 2013/0053675 A1 | 2/2013 | Kim et al. | |
| 2013/0211271 A1 | 8/2013 | Kang et al. | |
| 2013/0261482 A1 | 10/2013 | Marziliano et al. | |
| 2014/0094675 A1 | 4/2014 | Luna et al. | |
| 2014/0213863 A1 | 7/2014 | Loseu et al. | |
| 2014/0228650 A1 | 8/2014 | Ko et al. | |
| 2014/0276119 A1* | 9/2014 | Venkatraman | A61B 5/721 600/479 |
| 2016/0022220 A1* | 1/2016 | Lee | A61B 5/721 600/479 |
| 2016/0302679 A1* | 10/2016 | De Haan | A61B 5/7203 |

FOREIGN PATENT DOCUMENTS

| | | |
|---|---|---|
| CN | 102625667 A | 8/2012 |
| CN | 102949188 A | 3/2013 |
| CN | 103340621 A | 10/2013 |
| CN | 103596491 A | 2/2014 |
| CN | 103919536 A | 7/2014 |
| CN | 103976726 A | 8/2014 |
| CN | 104168821 A | 11/2014 |
| EP | 2338413 A | 6/2011 |
| EP | 2465419 A1 | 6/2012 |
| JP | 2012-518515 | 8/2012 |
| JP | 2015-16188 | 1/2015 |
| WO | 2007100959 A2 | 9/2007 |
| WO | 2010149726 A2 | 12/2010 |
| WO | 2012100175 A1 | 7/2012 |
| WO | 2013179018 A1 | 12/2013 |
| WO | WO 2014/020484 A2 | 2/2014 |

OTHER PUBLICATIONS

Notification Concerning Transmittal of International Preliminary Report on Patentability for International Application No. PCT/SG2014/000615, "Device and Method for Removal of Artifacts in Physiological Measurements", dated Jul. 6, 2017.

Shimazaki, T., et al., "Cancellation of Motion Artifact Induced by Exercise for PPG-Based Heart Rate Sensing", *Engineering in Medicine and Biology Society (EMBC)*, 2014, 36$^{th}$ Annual International Conference of the IEEE, pp. 3216-3219, Aug. 26-30, 2014.

Sweeney, K.T., et al., Artifact Removal in Physiological Signals—Practices and Possibililties', IEEE Transactions on Information Technology in Biomedicine, vol. 16, No. 3, May 2012.

Wood, L.B., et al., "Low Variance Adaptive Filter for Cancelling Motion Artifact in Wearable Photoplethysmogram Sensor Signals", *Engineering in Medicine and Biology Society*, 2007, 29$^{th}$ Annual International Conference of the IEEE, pp. 652-655, Aug. 22-26, 2007.

Written Opinion of the International Searching Authority for International Application No. PCT/SG2014/000615, "Device and Method for Removal of Artifacts in Physiological Measurements", dated Feb. 18, 2015.

\* cited by examiner

US 11,045,101 B2

DEVICE AND METHOD FOR REMOVAL OF ARTIFACTS IN PHYSIOLOGICAL MEASUREMENTS

This application is the U.S. National Stage of International Application No. PCT/SG2014/000615, filed Dec. 23, 2014, which designates the U.S., published in English. The entire teachings of the above application is incorporated herein by reference.

FIELD OF INVENTION

The present invention relates broadly to device and method for removal of artifacts in physiological measurements.

BACKGROUND

Physiological sensors are generally highly sensitive to motion artifacts. An example of such sensors is a photoplethysmography (PPG) sensor. A PPG sensor relies on the light emitting diodes and photo detectors to produce a PPG signal that can be used to monitor various parameters, such as heart rate and oxygen saturation level in blood. Therefore, it would not be desirable that the measurement unit utilizes a PPG signal that is corrupted by motion artifacts.

One way to detect motion artifacts in a PPG signal from a device is to incorporate an accelerometer (ACC) sensor, preferably a tri-axial ACC, to detect whether motion is present. With the tri-axial ACC sensor, the device can sense more specifically how the motion is along each axis and thus, the output of the ACC sensor can be used as a reference indicative of motion artifacts in the PPG signal and to correct the PPG signal accordingly.

Adaptive filtering with motion signals captured by ACC provides a promising method for the removal of artifacts from PPG data distorted by motion. However, there are cases when the ACC signals are not correlated with the PPG distortion, and in such cases the signal quality of the PPG will deteriorate after filtering with the ACC signal as noise reference.

WO2014020484 discloses a method of PPG signal motion artefact removal by first labelling the PPG signal with corresponding motion characteristics derived from ACC signals on beat by beat or second by second basis. It further discloses that PPG measurements which are labelled with acceptable motion characteristics are selected for further processing and lastly, motion free PPG measurements are generated by averaging PPG data that are labelled motion-free.

US20140276119 discloses a method of PPG signal motion artefact removal by first determining the activity state of the user, either through user input or inferred by ACC signals. If the user is engaging in an activity, adaptive filter predicts the PPG signal from the ACC signal on the basis of the motion artefact being the only component common to both signals.

US20140213863 discloses a method of PPG signal motion artefact removal by capturing a PPG signal using a first light emitting diode (LED) of the PPG heart rate monitor device, capturing a reference signal using a second LED of the PPG heart rate monitor device, wherein a wavelength of the second LED is complementary to the wavelength of the first LED, using the reference signal to remove motion noise from the PPG signal, wherein a motion noise compensated PPG signal is generated, and estimating a heart rate using the motion noise compensated PPG signal.

Embodiments of the present invention provide at least an alternative system and method for removal of artifacts in physiological measurements.

SUMMARY

In accordance with a first aspect of the present invention there is provided a method for removal of artifacts in physiological measurements, the method comprising the steps of obtaining a physiological signal of a user; obtaining corresponding motion data representative of motion of the user; detecting two or more motion cycles in the motion data; constructing a noise reference based on segments of the physiological signal corresponding to the two or more motion cycles respectively, and filtering the physiological signal with the noise reference.

In accordance with a second aspect of the present invention there is provided a device for removal of artifacts in physiological measurements, the device comprising a first sensor for obtaining a physiological signal of a user; a second sensor for obtaining corresponding motion data representative of motion of the user; and a processor for detecting two or more motion cycles in the motion data, constructing a noise reference based on segments of the physiological signal corresponding to the two or more motion cycles respectively, and filtering the physiological signal with the noise reference.

BRIEF DESCRIPTION OF THE DRAWINGS

Embodiments of the invention will be better understood and readily apparent to one of ordinary skill in the art from the following written description, by way of example only, and in conjunction with the drawings, in which.

DETAILED DESCRIPTION

Figure 1:
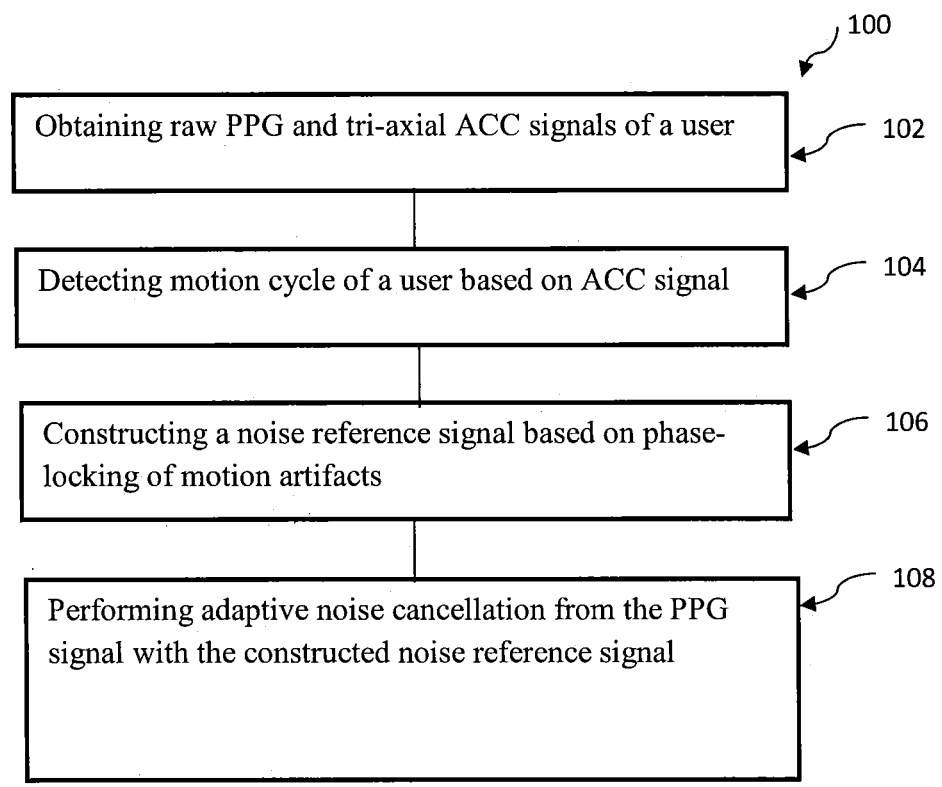
FIG. 1 shows a flow chart illustrating a method of removing artifacts in physiological measurements according to an example embodiment.

Embodiments of the present invention provide a method and system for determining a noise reference that is preferably well correlated with motion artifacts in PPG under rhythmic motions, for adaptive filtering In other words, embodiments of the present invention can provide a method for eliminating undesired artifacts in physiological measurements due to rhythmic body motions. Specifically, an embodiment of the invention relates to a method for the removal of motion artifacts from PPG signals from wearable sensors with an integrated tri-axial ACC. From the ACC signals, the device can detect more specifically the motion cycles of the user based on his/her activity and construct a noise reference based on the phase-locked artifact component of PPG data and thus, the constructed noise reference can be referenced on a level of motion of the user and correct the PPG signal accordingly. Such an embodiment of the present invention is advantageously able to achieve optimal or near optimal performance while being computationally inexpensive.

The present specification also discloses an apparatus, which may be internal and/or external to the wearable device in example embodiments, for performing the operations of the methods. Such apparatus may be specially constructed for the required purposes, or may comprise a general purpose computer or other device selectively activated or reconfigured by a computer program stored in the computer. The algorithms and displays presented herein are not inherently related to any particular computer or other apparatus. Various general purpose machines may be used with programs in accordance with the teachings herein. Alternatively, the construction of more specialized apparatus to perform the required method steps may be appropriate. The structure of a conventional general purpose computer will appear from the description below. In addition, the present specification also implicitly discloses a computer program, in that it would be apparent to the person skilled in the art that the individual steps of the method described herein may be put into effect by computer code. The computer program is not intended to be limited to any particular programming language and implementation thereof. It will be appreciated that a variety of programming languages and coding thereof may be used to implement the teachings of the disclosure contained herein. Moreover, the computer program is not intended to be limited to any particular control flow. There are many other variants of the computer program, which can use different control flows without departing from the spirit or scope of the invention.

Furthermore, one or more of the steps of the computer program may be performed in parallel rather than sequentially. Such a computer program may be stored on any computer readable medium. The computer readable medium may include storage devices such as magnetic or optical disks, memory chips, or other storage devices suitable for interfacing with a general purpose computer. The computer readable medium may also include a hard-wired medium such as exemplified in the Internet system, or wireless medium such as exemplified in the GSM mobile telephone system. The computer program when loaded and executed on such a general-purpose computer effectively results in an apparatus that implements the steps of the preferred method.

The invention may also be implemented as hardware modules. More particularly, in the hardware sense, a module is a functional hardware unit designed for use with other components or modules. For example, a module may be implemented using discrete electronic components, or it can form a portion of an entire electronic circuit such as an Application Specific Integrated Circuit (ASIC). Numerous other possibilities exist. Those skilled in the art will appreciate that the system can also be implemented as a combination of hardware and software modules.

The described embodiments of the invention described herein relate to a wearable device and a method for removal of motion artifacts from a physiological signal, based on motion signals acquired from the user with a motion sensor such as an ACC and/or a gyroscope.

In one embodiment, the device can be worn on any location of the user with sufficient skin area to allow the light emitting diode-photo detector (LED-PD) arrangement to acquire the PPG signal and allows the tri-axial ACC to acquire motion signals.

FIG. 1 shows a flow chart 100 illustrating a method of removing artifacts in physiological measurements according to an example embodiment, comprising the steps of:

Obtaining raw PPG and tri-axial ACC signals of a user, step 102.

Detecting two or more motion cycles of a user based on ACC signal, step 104.

Constructing a noise reference signal based on phase-locking of motion artifacts, step 106.

Performing adaptive noise cancellation from the PPG signal with the noise reference signal constructed based on the phase-locked artifact component data, step 108.

Details of the method illustrated in FIG. 1 according to the example embodiment will now be described.

Detecting Motion Cycle of a User Based on ACC Signal (Step 104, FIG. 1)

Figure 2:
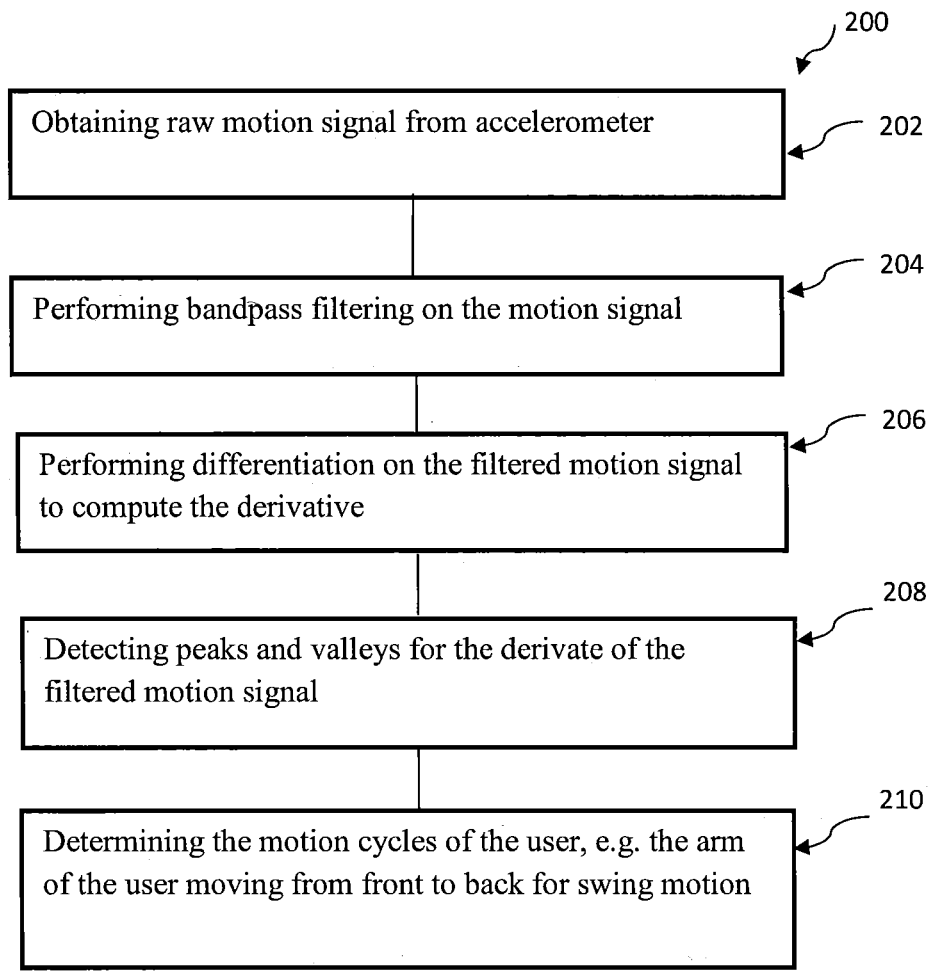
FIG. 2 shows a flow chart illustrating details of the method of removing artifacts in physiological measurements according to the example embodiment.
Figure 4:
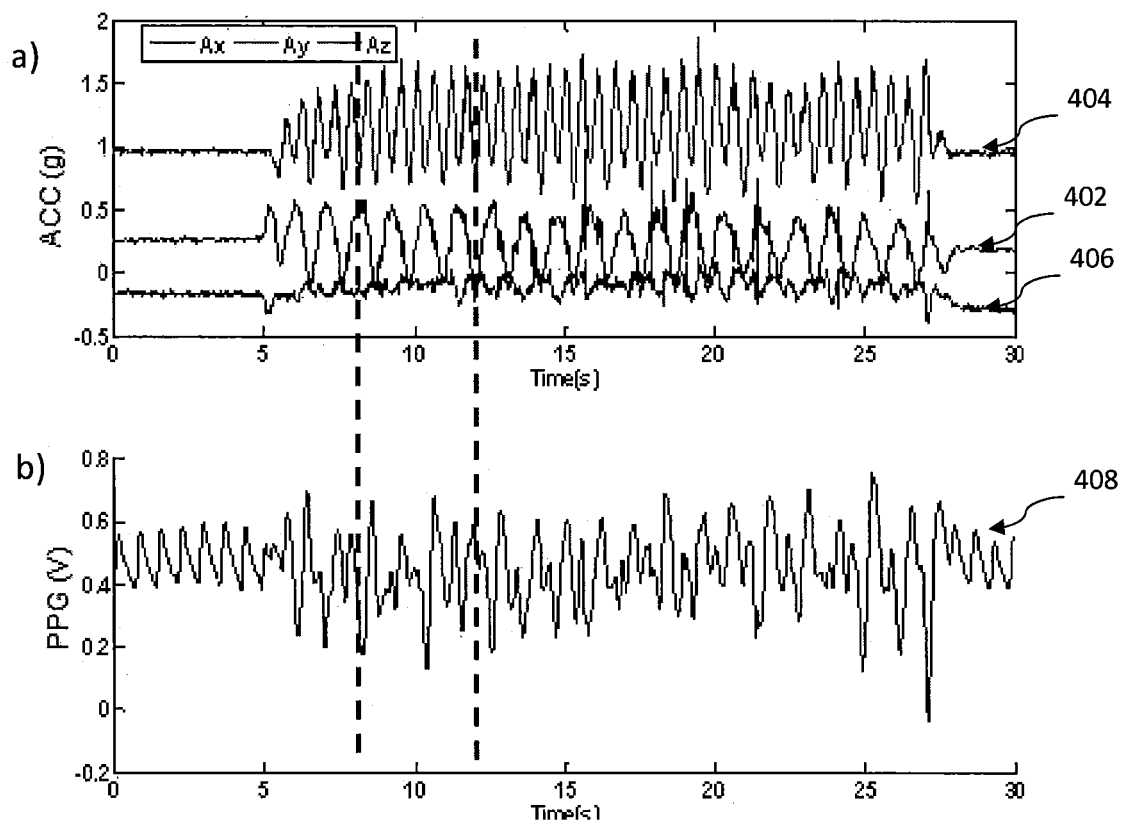
FIG. 4a) shows a graph illustrating obtained tri-axial ACC signals Ax, Ay and Az in the example embodiment.
FIG. 4b) shows a graph illustrating obtained a PPG signal simultaneously recorded with the tri-axial ACC signals in the example embodiment.

The method of detecting the user's motion cycle based on the ACC signal is shown in FIG. 2, and comprises:

Obtaining raw motion signal from an accelerometer, step 202. An example of obtained tri-axial ACC signals Ax, Ay and Az (corresponding respectively to an x-, y- and z-axis of the accelerometer of gyroscope) is shown in FIG. 4a), curves 402, 404 and 406. The corresponding obtained PPG signal 408 is shown in FIG. 4b). For tri-axial ACC signals, the ACC signal along the most active axis (i.e. the one with maximal g-force) is selected for motion cycle detection in this embodiment. However, in different embodiments, one or more of the ACC signals can be used to obtain the motion data for motion cycle detection.

Performing bandpass filtering on the motion signal, step 204. An example of a preferred range for the passband of the filter is 0.5-8 Hz.

Performing differentiation on the filtered motion signal to compute the derivative, step 206.

Detecting peaks and valleys for the derivate of the filtered motion signal, step 208.

Figure 5:
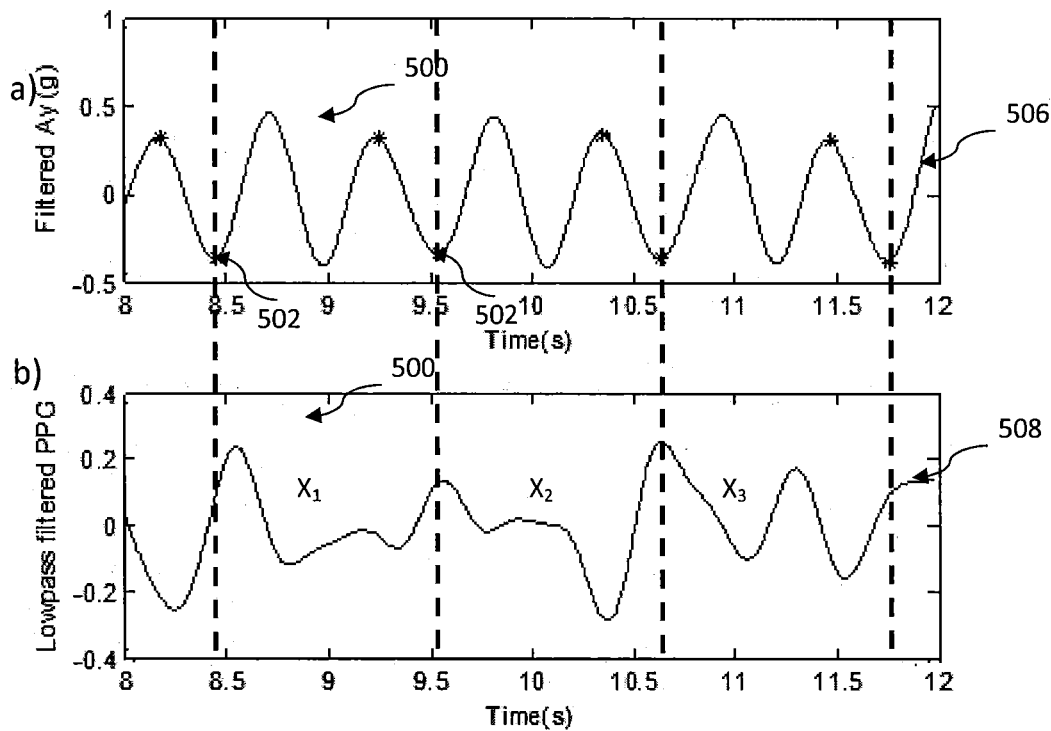
FIG. 5a) shows a graph illustrating detection of motion cycles in the example embodiment FIG. 5b) shows a graph illustrating segmenting the PPG signal in the example embodiment.

At step 210, the motion cycles of the user are determined to determine swing motion of e.g. the arm of the user from front to back. One motion cycle corresponds to the window e.g. 500 between two second next consecutive valleys e.g. 502, 504 or peaks of the derivative of the filtered motion signal 506 as shown in FIG. 5*a*) in the example embodiment.

Constructing the Noise Reference Signal Based on Phase-Locking of Motion Artifacts (Step 106, FIG. 1)

Figure 3:
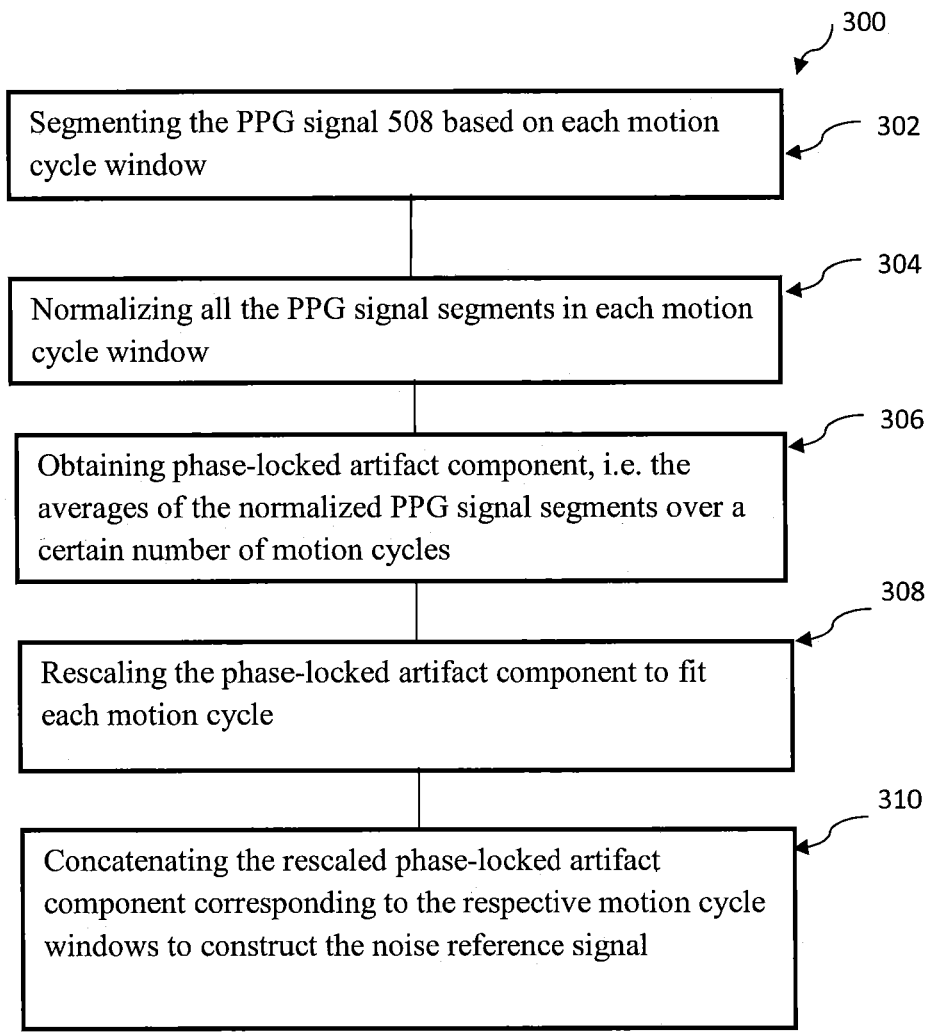
FIG. 3 shows a flow chart illustrating details of the method of removing artifacts in physiological measurements according to the example embodiment.

The method of constructing the noise reference signal in the example embodiment is shown in FIG. 3 and comprises:

At step 302, segmenting the PPG signal 508 based on each motion cycle window, $X_1, X_2, \ldots, X_L$, e.g. 500 as shown in FIG. 5*b*) is performed.

At step 304, normalizing the PPG signal segments e.g. 510 in each motion cycle window, $X_1', X_2', \ldots, X_L'$, e.g. 500 in time is performed.

At step 306, obtaining averages of the normalized PPG signal segments e.g. 510 over a certain number of motion cycles is performed, to obtain the phase-locked artifact component, $N_a$, for construction of a noise reference. As a result of the averaging of the normalized PPG signal segments e.g. 510 in the example embodiment, the artifact component is enhanced while the actual PPG component, $S_1, S_2, \ldots, S_L$, is suppressed. This is because the actual PPG component can be expected to be out-of-phase between the different normalized PPG signal segments e.g. 510, since segmentation is based on the detected motion cycle windows e.g. 500, which are typically not synchronized with the actual PPG characteristics (i.e. the cardiac cycle). On the other hand, motion artifacts in the PPG signal can be expected to be in-phase between the different normalized PPG signal segments e.g. 510. Therefore, the obtained average of the PPG segments can advantageously be expected to be representative of mainly, preferably only, the motion artifacts in the PPG signal.

In one example, the processing of the PPG signal segments is performed using the following algorithms:

a) normalization in time:
Given a PPG segment corresponding to a motion cycle $X_i = [x_{i,0}, x_{i,1}, \ldots, x_{i,M}]$ with sampling times $T = [t_0, t_1, \ldots, t_M]$, the normalization process involves
i. linearly resealing the sampling times of $X_i$ to be between 0 and 1, $T' = [t_0', t_1', \ldots, t_M']$, where $$t_j' = (t_j - t_0)/(t_M - t_0), j = 1, 2, \ldots, M. \quad (1)$$

ii. resampling the resealed PPG segment at a interval of $1/N$ by linear interpolation, $X_i' = [x_{i,0}', x_{i,1}', \ldots, x_{i,N}']$, where $$x_{i,j}' = x_{i,k} + (x_{i,k+1} - x_{i,k})*(j*M/N - k), k/M \leq j/N \leq (k+1)/M. \quad (2)$$

b) averaging:
Given normalized PPG segments, $X_1', X_2', X_L'$, corresponding to L motion cycles, the average over these PPG segments is obtained as $$X_a = (X_1' + X_2' + \ldots + X_L')/L = (S_1 + S_2 + \ldots + S_L)/L + N_a \approx N_a. \quad (3)$$

The number of motion cycles sufficient to obtain a reliable estimate of motion artifacts will depend e.g. on the level of motion artifacts in the PPG signal. It was found by the inventors that a reliable estimate of motion artifacts can be obtained from a small number of motion cycles (even 2 cycles) when motion artifacts are high in the PPG, i.e. when motion intensity is high. The motion intensity can e.g. be determined based on the number of motion cycles per second or the magnitude of motion signals. This advantageously enables example embodiments to be capable of handling large motion artifacts during high-intensity rhythmic activities. The number of motion cycles can for example be pre-set for a user selected activity and/or can be automatically set according to the motion intensity determined from the motion signals.

Figure 6:
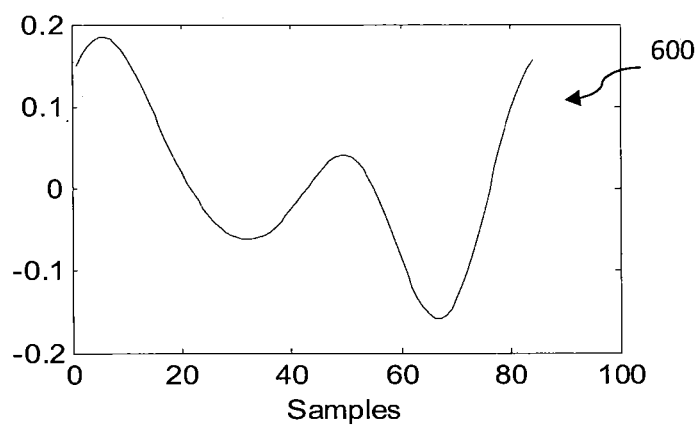
FIG. 6 shows a graph illustrating the phase-locked artifact component in the example embodiment.

At step 308, the phase-locked artifact component 600 (FIG. 6) is rescaled in time to fit into the respective motion cycle windows e.g. 500 (FIG. 5), resulting in respective rescaled versions of the phase-locked artifact component 600 fitting into the respective motion cycle windows e.g. 500.

Figure 7:
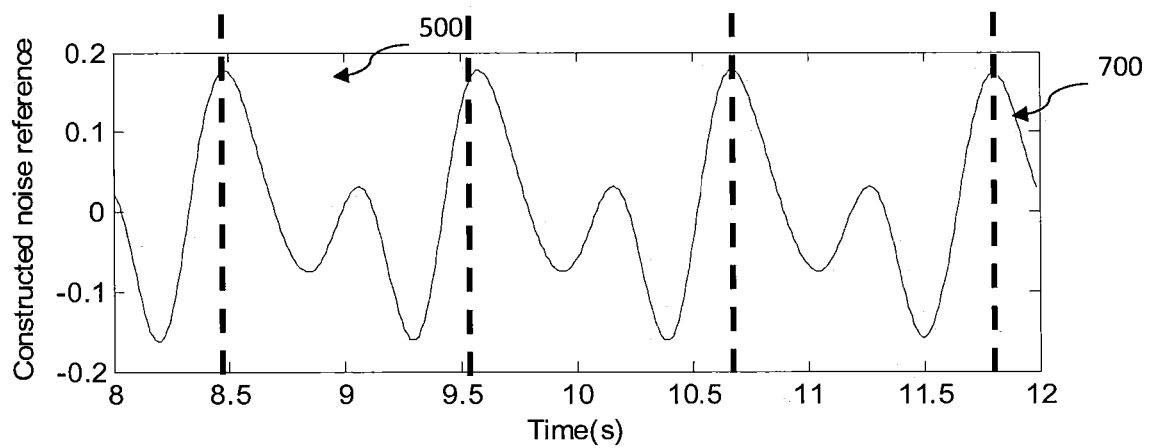
FIG. 7 shows a graph illustrating concatenation of the resealed phase-locked artifact component according to the respective motion cycles in the example embodiment.

At step 310, the respective resealed versions of phase-locked artifact component corresponding to the respective motion cycle windows e.g. 500 are concatenated/stitched together to construct the noise reference signal 700, as shown in FIG. 7. Accordingly, the constructed noise reference signal 700 corresponds in time to the same sequence of motion cycle windows e.g. 500 in the obtained PPG signal and the motion signal, compare e.g. FIG. 4.

Performing Adaptive Noise Cancellation from the PPG Signal with the Noise Reference Signal Constructed Based on Phase-Locked Artifact Component (Step 108, FIG. 1)

The method of performing adaptive noise cancellation can be any existing algorithm, including, but not limited to:
1. Least-mean-square (LMS) algorithm.
2. Recursive-least-square (RLS) algorithm.

Figure 8:
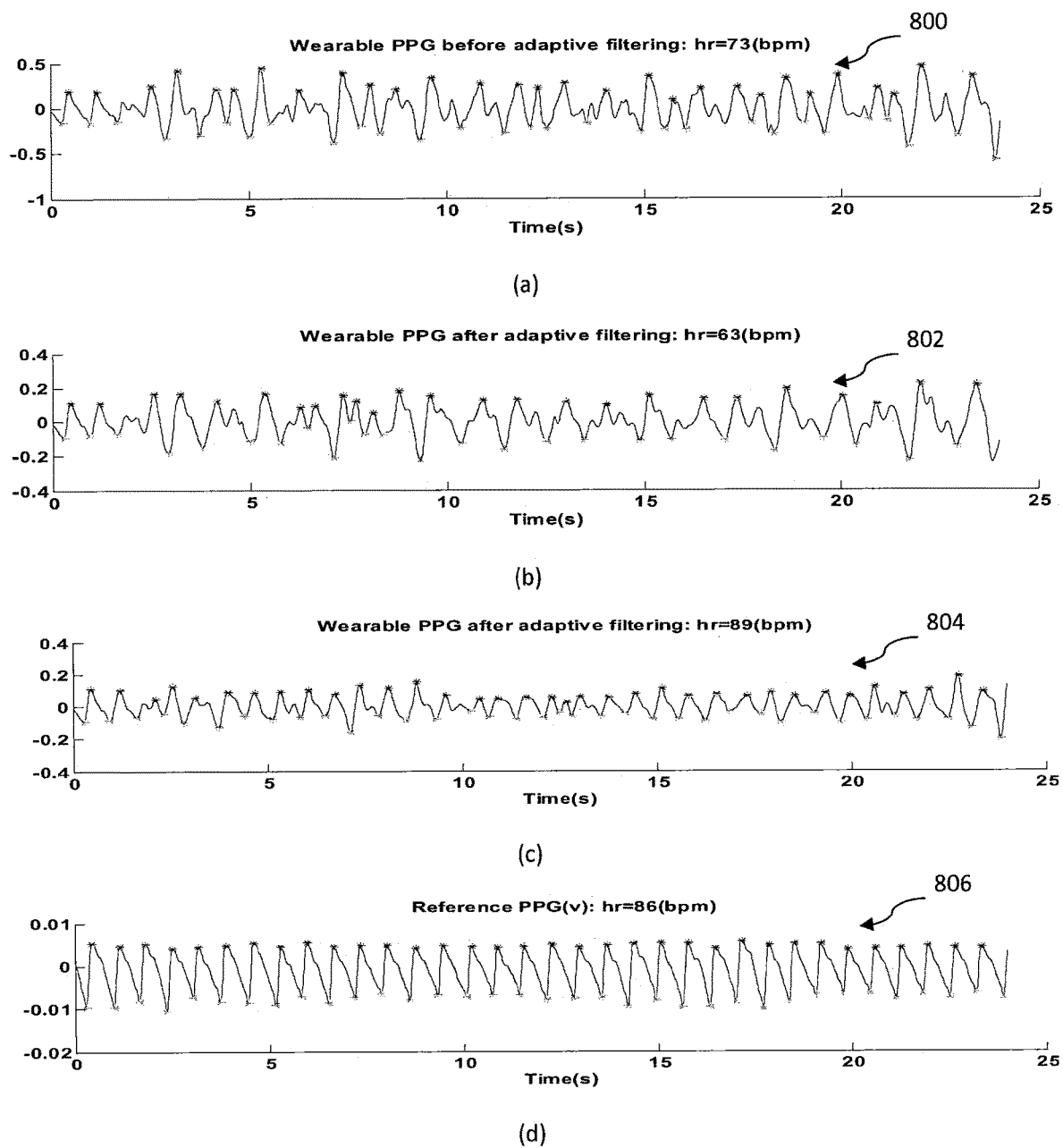
FIG. 8a) shows a graph illustrating a PPG signal recorded from the wrist of a wearer with the arm swinging to resemble a walking condition in an example embodiment.
FIG. 8b) shows a graph illustrating the PPG signal of FIG. 8a) after artifact removal by adaptive filtering with the ACC signal as prior art noise reference.
FIG. 8c) shows a graph illustrating the PPG signal of FIG. 8a) after artifact removal using a noise reference obtained according to an example embodiment.
FIG. 8d) shows a PPG signal recorded from the index finger of the stationary other hand of the wearer.

FIGS. 8*a*)-*d*) show a comparison of removal of artifacts according to an example embodiment to a method using the ACC signal as noise reference for adaptive filtering, based on PPG recordings with one arm swinging to resemble a walking condition and the other arm being kept stationary. FIG. 8*a*) shows the PPG signal 800 recorded from the wrist of the moving arm. FIGS. 8*b*) and 8*c*) show the PPG signal after artifact removal by adaptive filtering with the ACC signal as noise reference (signal 802) and the PPG signal after artifact removal by the method in the example embodiment (signal 804), respectively. FIG. 8*d*) shows the PPG signal recorded from the index finger of the stationary arm as a reference PPG signal 806. As can be seen, both the waveform and the peak positions of the PPG signal 804 (FIG. 8*c*) are much closer to the reference PPG signal 806 (FIG. 8*d*) as compared to those of the PPG signal 802 in FIG. 8*b*). This demonstrates the improved performance of the method in the example embodiment over the method using the ACC signal as noise reference in particular, and the overall good performance as illustrated by the close similarity to the reference PPG signal 806 (FIG. 8*d*).

As will be appreciated by a person skilled in the art, the computation involved in the example embodiments described mainly include simple derivation, peak detection, averaging and resealing processing which is inexpensive and thus there will be negligible time delay and power consumption for this processing.

Figure 9:
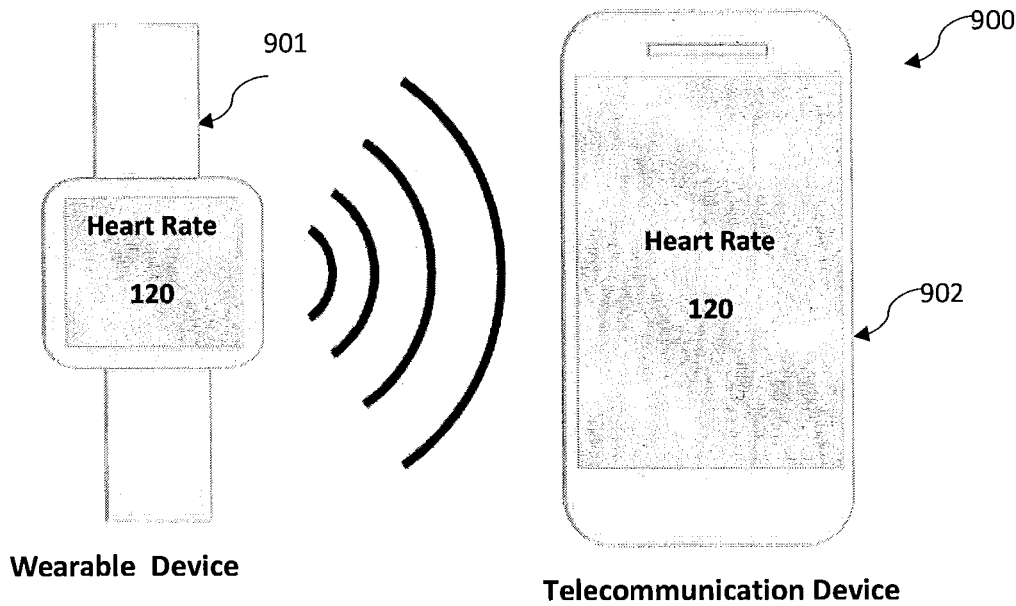
FIG. 9 shows a schematic diagram illustrating an assembly comprising a wearable device in the form of a wrist watch according to an example embodiment.

FIG. 9 shows an assembly 900 comprising a wearable device in the form of a wrist watch 901 according to an example embodiment. It will be appreciated that in different embodiments the device may also be in any other form suitable to be worn on any part of the user's body such as his/her arms, waist, hip or foot. The wrist watch 901 obtains physiological measurements and motion data from a user, removes artifacts in the physiological measurements, processes the data and displays result(s) and communicates the result(s) wirelessly to a telecommunication device of the assembly 900 such as a mobile phone 902 or other portable electronic devices, or computing devices such as desk top computers, laptop computer, tab computers etc.

Figure 10:
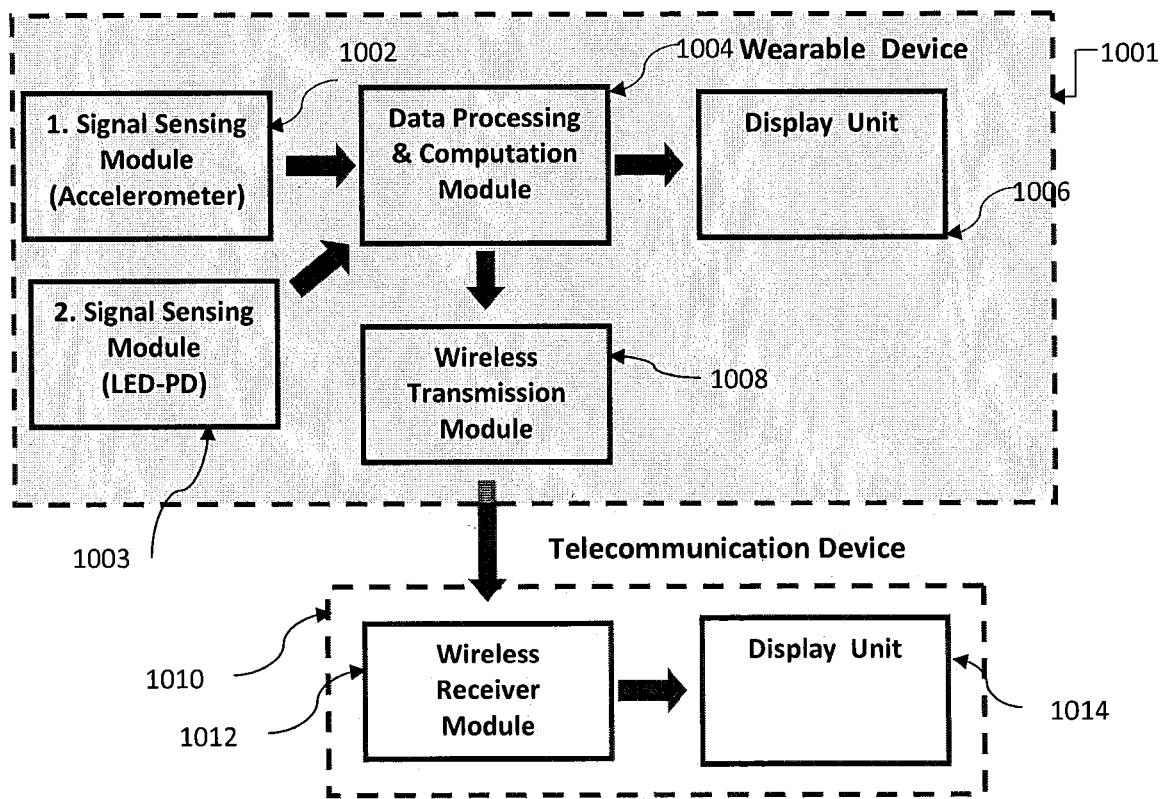
FIG. 10 shows a schematic block diagram illustrating an assembly comprising a wearable device according to an example embodiment.

FIG. 10 shows a schematic block diagram of an assembly 1000 comprising a wearable device 1001 according to an example embodiment, for obtaining physiological measurements from a user and removing artifacts in the physiological measurements. The device 1001 includes a first signal sensing module 1002, such as an accelerometer or gyroscope, for obtaining the motion information of the user.

One non-limiting example of a preferred accelerometer that can be adapted for use in the device is a triple-axis accelerometer MMA8652FC available from Freescale Semiconductor, Inc. This accelerometer can provide the advantage of measuring acceleration in all three directions with a single package. Alternatively, several single-axis accelerometers oriented to provide three-axis sensing can be used in different embodiments.

The device 1001 also includes a second sensing module 1003, such as an LED-PD module, for obtaining a physiological signal of the user. The device 1001 also includes a data processing and computational module 1004, such as a processor, which is arranged to receive and process the acceleration information from the signal sensing module 1002 and the physiological signal from the measurement module 1003. The device 1001 also includes a display unit 1006 for displaying a result to a user of the device 1001 and for receiving user input via touch screen technology. The device 1001 in this embodiment further includes a wireless transmission module 1008 arranged to communicate wirelessly with a telecommunications device 1010 of the assembly 1000. The telecommunication device 1010 includes a wireless receiver module 1012 for receiving signals from the wearable device 1001, a display unit 1014 for displaying a result to a user of the telecommunication device 1010 and for receiving user input via touch screen technology.

Figure 11:
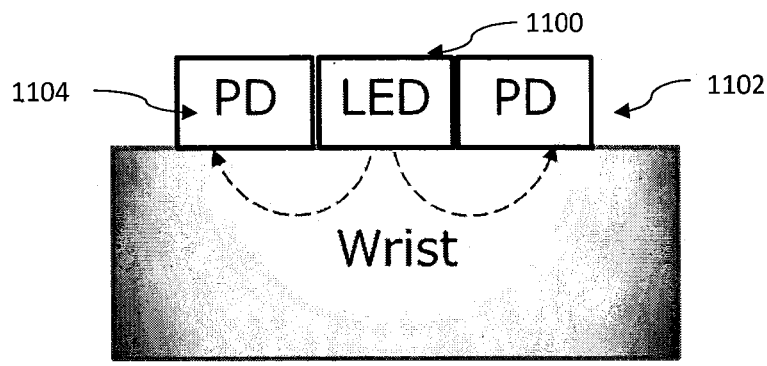
FIG. 11 shows a schematic diagram illustrating a preferred LED-PD configuration for the measurement in reflectance mode for a wearable device of FIG. 9.

FIG. 11 shows a schematic illustration of preferred LED-PD configuration for the measurement in reflectance mode for a wearable device in the form of wrist watch 1101. The measurement is based on the amount of light by a LED 1100 reflected back to two PDs 1102, 1104. One non-limiting example of a preferred LED-PD module that can be adapted for use in the device is composed of one LED, e.g. One-White Surface Mount PLCC-2 LED Indicator ASMT-UWB1-NX302, paired with one or multiple PDs, e.g. ambient light sensor TEMD5510FX01. Alternatively, the LED-PD module can be composed of multiple LEDs paired with one or multiple PDs.

Figure 12:
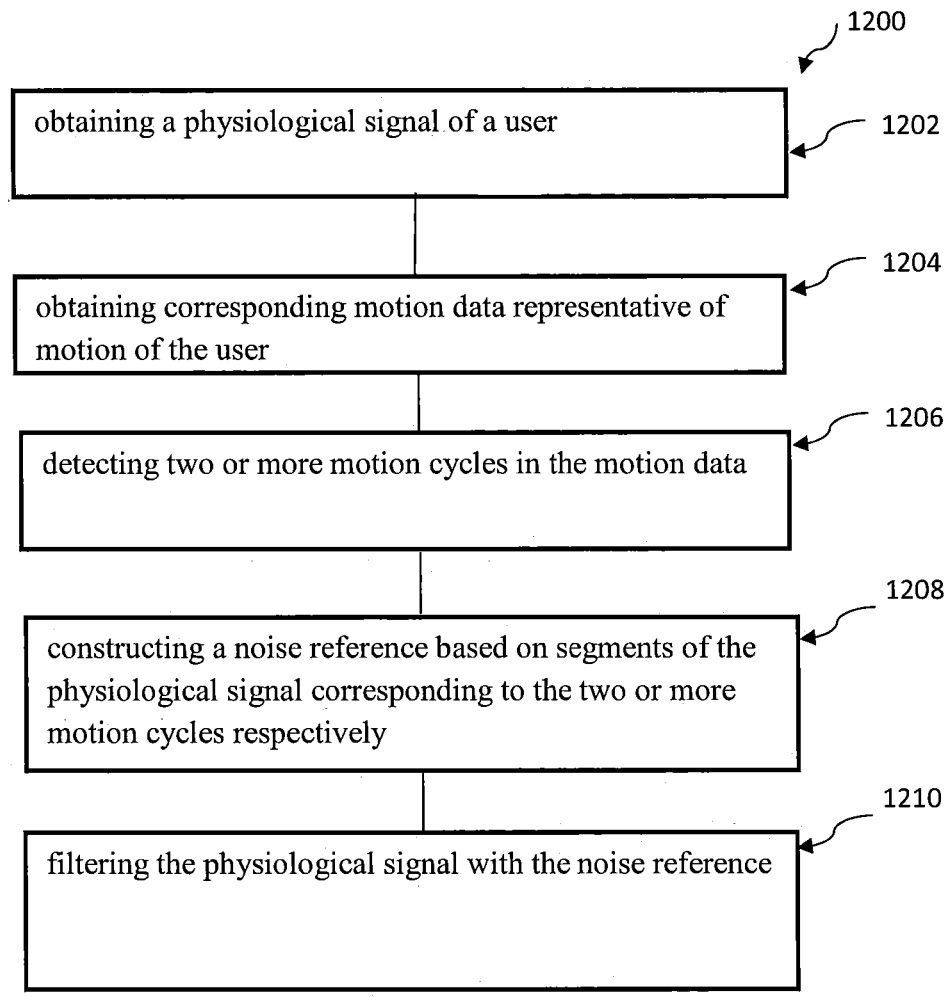
FIG. 12 shows a flowchart illustrating a method for removal, of artifacts in physiological measurements, according to one embodiment.

FIG. 12 shows a flowchart 1200 illustrating a method for removal of artifacts in physiological measurements, according to one embodiment. At step 1202, a physiological signal of a user is obtained. At step 1204, corresponding motion data representative of motion of the user is obtained. At step 1206, two or more motion cycles in the motion data are detected. At step 1208, a noise reference is constructed based on segments of the physiological signal corresponding to the two or more motion cycles respectively. At step 1210, the physiological signal is filtered with the noise reference.

Detecting two or more motion cycles in the motion data may comprise bandpass filtering the motion data. Detecting two or more motion cycles in the motion data may further comprise performing differentiation on the filtered motion signal to compute a derivative of the filtered motion data. Detecting two or more motion cycles in the motion data may further comprise detecting peaks or valleys in the derivative of the filtered motion data. Detecting two or more motion cycles in the motion data may further comprise detecting segments of the motion data between two peaks or valleys as respective motion cycles. The two peaks or valleys associated with the respective segments may be second next consecutive peaks or valleys.

Constructing the noise reference based on the segments of the physiological signal may comprise enhancing motion artifacts.

Constructing the noise reference based on the segments of the physiological signal may comprise suppressing a physiological component.

Constructing the noise reference based on the segments of the physiological signal may comprise normalizing the segments of the physiological signal in time. Constructing the noise reference based on the segments of the physiological signal may further comprise obtaining an average of the normalized segments of the physiological signal as phase-locked artifact component. Obtaining the average of the normalized segments of the physiological signal may comprise suppressing out-of-phase components between the normalized segments of the physiological signal. Obtaining the average of the normalized segments of the physiological signal may comprise enhancing in-phase components between the normalized segments of the physiological signal. Constructing the noise reference based on the segments of the physiological signal may further comprise re-scaling the phase-locked artifact component to correspond to the respective segments of the physiological signal. Constructing the noise reference based on the segments of the physiological signal may further comprise concatenating or stitching together the respective re-scaled phase-locked artifact component corresponding to the respective motion cycle windows.

The obtained corresponding motion data may comprise tri-axial motion signals. Detecting the two or more motion cycles may be based on one or more of the tri-axial motion signals.

The method may further comprise setting a number of the motion cycles to be detected for the construction of the noise reference. Setting the number may be based on user input. The setting the number may comprise determining an intensity of the motion based on the motion data.

Filtering the physiological signal with the noise reference may comprise applying a least-mean-square (LMS) algorithm, a recursive-least-square (RLS) algorithm, or the like.

Figure 13:
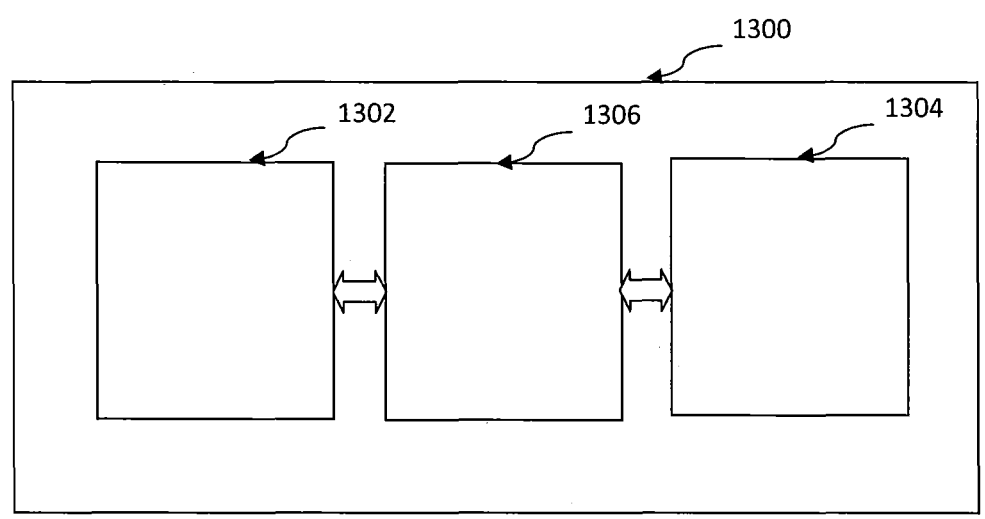
FIG. 13 shows a schematic block diagram illustrating a device for removal of artifacts in physiological measurements, according to one embodiment.

FIG. 13 shows a schematic block diagram illustrating a device 1300 for removal of artifacts in physiological measurements, according to one embodiment. The device 1300 comprises a first sensor 1302 for obtaining a physiological signal of a user, a second sensor 1304 for obtaining corresponding motion data representative of motion of the user, and a processor 1306 for detecting two or more motion cycles in the motion data, constructing a noise reference based on segments of the physiological signal corresponding to the two or more motion cycles respectively, and filtering the physiological signal with the noise reference.

Detecting two or more motion cycles in the motion data may comprise bandpass filtering the motion data. Detecting two or more motion cycles in the motion data may further comprise performing differentiation on the filtered motion signal to compute a derivative of the filtered motion data. Detecting two or more motion cycles in the motion data may further comprise detecting peaks or valleys in the derivative of the filtered motion data. Detecting two or more motion cycles in the motion data may further comprise detecting segments of the motion data between two peaks or valleys as respective motion cycles. The two peaks or valleys associated with the respective segments may be second next consecutive peaks or valleys.

Constructing the noise reference based on the segments of the physiological signal may comprise enhancing motion artifacts.

Constructing the noise reference based on the segments of the physiological signal may comprise suppressing a physiological component.

Constructing the noise reference based on the segments of the physiological signal may comprise normalizing the segments of the physiological signal in time. Constructing the noise reference based on the segments of the physiological signal may further comprise obtaining an average of the normalized segments of the physiological signal as phase-locked artifact component. Obtaining the average of the normalized segments of the physiological signal may comprise suppressing out-of-phase components between the normalized segments of the physiological signal. Obtaining the average of the normalized segments of the physiological signal may comprise enhancing in-phase components between the normalized segments of the physiological signal. Constructing the noise reference based on the segments of the physiological signal may further comprise re-scaling the phase-locked artifact component to correspond to the respective segments of the physiological signal. Constructing the noise reference based on the segments of the physiological signal may further comprise concatenating or stitching together the respective re-scaled phase-locked artifact component corresponding to the respective motion cycle window.

The obtained corresponding motion data may comprise tri-axial motion signals. Detecting the two or more motion cycles may be based on one or more of the tri-axial motion signals.

The processor 1306 may further be configured for setting a number of the motion cycles to be detected for the construction of the noise reference. Setting the number may be based on user input. The setting the number may comprise determining an intensity of the motion based on the motion data.

Filtering the physiological signal with the noise reference may comprise applying a least-mean-square (LMS) algorithm, a recursive-least-square (RLS) algorithm, or the like.

It will be appreciated by a person skilled in the art that numerous variations and/or modifications may be made to the present invention as shown in the specific embodiments without departing from the spirit or scope of the invention as broadly described. The present embodiments are, therefore, to be considered in all respects to be illustrative and not restrictive. Also, the invention includes any combination of features, in particular any combination of features in the patent claims, even if the feature or combination of features is not explicitly specified in the patent claims or the present embodiments.

For example, while a wrist-worn device is described in some embodiments, the device may be worn on any part of the arms, hip, waist or foot of the user.

Also, while rhythmic motion is being referred to herein, it will be appreciated that this term is not intended to impose any limitation on the motion as such other than that the motion consists of two or more substantially repetitive motion data patterns or signatures associated with the motion.

The invention claimed is:

1. A method for generating an electronic signal representing physiological measurements with artifacts in the physiological measurements removed, the method comprising:

obtaining, using a physiological measurement sensor integrated into a wearable device, an electronic physiological signal of a user;

obtaining, using an accelerometer integrated into the wearable device, corresponding electronic motion data representative of motion of the user;

determining, using a processor coupled to the physiological measurement sensor and the accelerometer, two or more motion cycles in the electronic motion data;

constructing, using the processor, an electronic noise reference based on segments of the electronic physiological signal corresponding to the two or more motion cycles respectively; and generating, using the processor, the electronic signal representing the physiological measurements with the artifacts in the physiological measurements removed by filtering the electronic physiological signal with the electronic noise reference;

wherein constructing, using the processor, the electronic noise reference comprises:

normalizing, using the processor, the segments of the physiological signal in time;

obtaining, using the processor, an average of the normalized segments of the physiological signal as a phase-locked artifact component;

re-scaling, using the processor, the phase-locked artifact component to generate rescaled versions of the phase-locked artifact component corresponding to the respective segments of the electronic physiological signal; and concatenating, using the processor, the respective re-scaled versions of the phase-locked artifact component.

2. The method as claimed in claim 1, wherein determining, using the processor, two or more motion cycles in the motion data comprises bandpass filtering, using the processor, the motion data to generate filtered motion data.

3. The method as claimed in claim 2, wherein determining, using the processor, two or more motion cycles in the motion data further comprises at least one of: a) performing differentiation, using the processor, on the filtered motion signal; b) determining, using the processor, peaks or valleys in a derivative of the filtered motion data; and c) determining, using the processor, segments of the motion data between two peaks or valleys as respective motion cycles.

4. The method as claimed in claim 1, wherein constructing, using the processor, the electronic noise reference based on the segments of the electronic physiological signal comprises enhancing motion artifacts.

5. The method as claimed in claim 1, wherein constructing, using the processor, the electronic noise reference based on the segments of the electronic physiological signal comprises suppressing a physiological component.

6. The method as claimed in claim 1, wherein obtaining the average of the normalized segments of the electronic physiological signal comprises enhancing in-phase components between the normalized segments of the electronic physiological signal.

7. The method as claimed in claim 1, wherein the obtained corresponding motion data comprises single-, dual- or multi-axial motion signals, and wherein determining the two or more motion cycles is based on one or more of the single-, dual- or multi-axial motion signals.

8. The method as claimed in claim 1, further comprising setting a number of the motion cycles to be determined for the construction of the electronic noise reference, wherein the setting the number is based on user input, and wherein the setting the number comprises determining an intensity of the motion based on the motion data.

9. The method as claimed in claim 1, wherein filtering, using the processor, the electronic physiological signal with the electronic noise reference comprises applying a least-mean-square (LMS) algorithm, or a recursive-least-square (RLS) algorithm.

10. A device for generating an electronic signal representing physiological measurements with artifacts in the physiological measurements removed, the device comprising:
- a physiological measurement sensor configured to obtain an electronic physiological signal of a user;
- an accelerometer configured to obtain corresponding motion data representative of motion of the user; and
- a processor coupled to the physiological measurement sensor and the accelerometer and configured to determine two or more motion cycles in the motion data, to construct an electronic noise reference based on segments of the electronic physiological signal corresponding to the two or more motion cycles respectively, and to generate the electronic signal representing the physiological measurements with the artifacts in the physiological measurements removed by filtering the electronic physiological signal with the electronic noise reference;
- wherein the processor is configured to construct the electronic noise reference by executing the steps of:
- normalizing the segments of the physiological signal in time;
- obtaining an average of the normalized segments of the physiological signal as a phase-locked artifact component;
- re-scaling the phase-locked artifact component to generate rescaled versions of the phase-locked artifact component corresponding to the respective segments of the electronic physiological signal; and
- concatenating the respective re-scaled versions of the phase-locked artifact component.

11. The device as claimed in claim 10, wherein determining two or more motion cycles in the motion data comprises bandpass filtering the motion data to generate filtered motion data.

12. The device as claimed in claim 11, wherein determining two or more motion cycles in the motion data further comprises at least one of: a) performing differentiation on the filtered electronic motion signal; b) determining peaks or valleys in a derivative of the filtered motion data; and c) determining segments of the motion data between two peaks or valleys as respective motion cycles.

13. The device as claimed in claim 10, wherein constructing the electronic noise reference based on the segments of the electronic physiological signal comprises enhancing motion artifacts.

14. The device as claimed in claim 10, wherein constructing the electronic noise reference based on the segments of the electronic physiological signal comprises suppressing a physiological component.

15. The device as claimed in claim 10, wherein obtaining the average of the normalized segments of the electronic physiological signal comprises enhancing in-phase components between the normalized segments of the electronic physiological signal.

16. The device as claimed in claim 10, wherein the obtained corresponding motion data comprises single-, dual- or multi-axial motion signals, and wherein determining the two or more motion cycles is based on one or more of the single-, dual- or multi-axial motion signals.

17. The device as claimed in claim 10, further comprising the processor being configured for setting a number of the motion cycles to be determined for the construction of the electronic noise reference, wherein the setting the number is based on user input, and wherein the setting the number comprises determining an intensity of the motion based on the motion data.

18. The device as claimed in claim 10, wherein filtering the electronic physiological signal with the noise reference comprises applying a least-mean-square (LMS) algorithm, or a recursive-least-square (RLS) algorithm.

* * * * *